United States Patent [19]

Schott et al.

[11] Patent Number: 5,679,652
[45] Date of Patent: Oct. 21, 1997

[54] AMPHIPHILIC NUCLEOSIDEPHOSPHATE ANALOGUES

[76] Inventors: Herbert Schott, Hartmeyerstrasse 14, D-72076 Tübingen, Germany; Albert Reto Schwendener, Mythenstrasse 1, CH-8802 Kilchberg, Switzerland; Frédérique Guérin, Am Zimmerplatz 16, D-66128 Saarbrücken, Germany

[21] Appl. No.: 284,683
[22] PCT Filed: Feb. 12, 1993
[86] PCT No.: PCT/EP93/00346
 § 371 Date: Jan. 27, 1995
 § 102(e) Date: Jan. 27, 1995
[87] PCT Pub. No.: WO93/16093
 PCT Pub. Date: Aug. 19, 1993

[30] Foreign Application Priority Data

Feb. 13, 1992 [DE] Germany .......... 42 04 211.9
Jul. 28, 1992 [DE] Germany .......... 42 24 878.7

[51] Int. Cl.$^6$ .......... A61K 31/505; C07H 19/06
[52] U.S. Cl. .......... 514/52; 514/49; 536/28.4; 536/28.5; 536/28.51
[58] Field of Search .......... 514/49, 52; 536/28.4, 536/28.5, 28.51; 544/243, 318, 296

[56] References Cited

FOREIGN PATENT DOCUMENTS 0392791 10/1990 European Pat. Off. .
9006319 6/1990 WIPO .

OTHER PUBLICATIONS

Furman et al., "Phosphorylation of 3'-azido-3'-deooxythymidine and selective interaction of the 5'-triphosphate with human immunodeficiency virus reverse transcriptase," *Proc. Natl. Acad. Sci. USA*, vol. 83, pp. 8333–8337, Nov. 1986.
CA85: 103772, 1996.
Cancer Res., 1976, 36(8) 2726–32.
Piet Herdewijn et al., "Synthesis and Anti-HIV Activity of Different Sugar–Modified Pyrimidine and Purine Nucleosides," *J. Med. Chem.*, 1988, 31, 2040–2048.

Primary Examiner—Yogendra N. Gupta
Attorney, Agent, or Firm—Rothwell, Figg, Ernst & Kurz, P.C.

[57] ABSTRACT

Amphiphilic nucleoside phosphate analogues of formula I

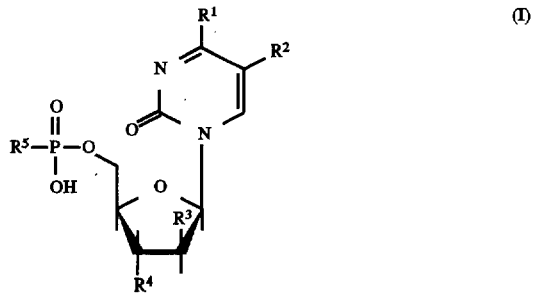

wherein $R^1$ denotes a hydroxyl or amino group or an acylated or alkylated or polyoxyethylene-substituted amino group, the acyl or alkyl group of which is straight-chained or branched, has 1 to 24 carbon atoms and up to 2 double bonds and may be substituted by an aromatic group;

$R^2$ denotes H, F, a 2-bromo vinyl group or a straight-chained or branched $C_{1-24}$-alkyl group;

$R^3$ and $R^4$ are identical or different and denote H, hydroxyl, halogen and azido; $R^5$ denotes a nucleoside group of formula II

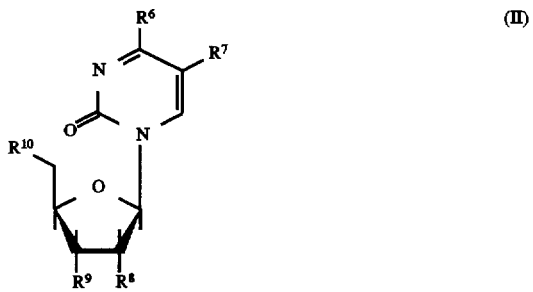

wherein $R^6$ denotes a hydroxyl or amino group or an acylated or alkalized amino group, the acyl or alkyl group of which is straight-chained or branched, contains 1 to 24 carbon atoms and up to 2 double bonds and may be substituted by an aromatic group, whilst $R^6$ and $R^1$ are different and one of the groups denotes acylamino or alkylamino groups having 12 to 24 carbon atoms, $R^1$, $R^2$, $R^6$ and $R^7$ are selected so that, together, they impart an amphiphilic nature to a dinucleotide phosphate analogue; and the corresponding salts of the acid forms of these compounds.

11 Claims, No Drawings

AMPHIPHILIC NUCLEOSIDEPHOSPHATE ANALOGUES

The present invention relates to new amphiphilic nucleosidephosphate analogues, the production of these, and means for treating cancer-type diseases and infectious diseases. Nucleoside analogues that have specific structural features are proven medications used in the therapies applied for cancer and infectious diseases caused by viruses (AIDS Res. Human Retroviruses 8, 119 (1992)). The therapeutic effect of cytosine nucleoside analogues, for example, araC is limited in that the body's cytosine desaminases desaminate the amino group of the nucleo-base too rapidly and the uracile nucleoside analogues that are formed thereby are, as a rule, therapeutically ineffective (Biochem. Pharmacol. 33, 2159 (1984)). In order to achieve a therapeutic effect, cytosinenucleoside analogues thus have to be applied in large doses that are associated with serious side effects for the patient. Attempts are being made to optimize the therapeutic effect with cytosinenucleoside analogues, the amino groups of which have protective groups.

3'-azido-2',3'-didesoxythymidine (AZT) and 2',3'-didesoxycytidine (ddC) are examples of the virostatics that are most frequently used for chemotherapy in the case of AIDS. The anti-retroviral effect is based on the fact that AZT and ddC are anabolized to the 5'-triphosphate derivate after cell absorption and these then selectively bind the reverse-transkriptase of the human immune deficiency virus (HIV), by which AIDS is triggered (Proc. Natl. Acad. Sci. U.S.A. 1986, 38, 8333–8337). Attempts have been made to increase the anti-HIV effect of AZT by using AZT derivatives, which are better absorbed by the infected cells or only liberate AZT after a delay (depot effect) because of inhibited hydrolysis, and to reduce the serious toxic side effects. According to another concept, attempts are being made to deliberately neutralize the large HIV reservoir of macrophages that have encapsulated AZT or glycerophospholipid-AZT-congugates in their lipid membrane. It is hoped that the macrophages will consume the greater part of the applied liposomes before they hydrolyse, so that only a small quantity of liberated AZT is absorbed by other cells, the toxic side effects being reduced by this. In a new therapy schema, with which the therapeutic index of AZT can be improved, AZT is being administered with 2',3'-didesoxycytidine (ddC). However, attempts are also being made to achieve the advantage of such a combination therapy using dinucleosidephosphate analogues, in which AZT is bound covalently with other anti-retroviral didesoxynucleoside analogues, although, however, the most effective nucleosides AZT and ddC have still not yet been coupled (AIDS Res. Human. Retro. 198, 4, 449–4547 Antimicrob. Agents Chemother. 1990, 34, 1061–1067). However, the dimerisation of different anti-retrovirally effective compounds is only useful if both reagents develop their effect in approximately equal concentrations. A considerable disadvantage of the dimers that have been described is their excessively hydrophilic character. Because of this, passage through the cell membrane and the stable incorporation in liposomes is made more difficult and enzymatic hydrolysis is not delayed.

It is the task of the present invent ion to describe new nucleosidephosphate analogues with which cancerous diseases and infections can be combatted more effectively.

This problem has been solved by new amphiphilic nucleosidephosphate analogues that combine the advantages of the various concepts referred to above, and are accessable in preparative quantities at reasonable cost. Lipophilic nucleotide derivatives have been covalently bonded to hydrophilic therapeutically effective nucleoside analogues through phosphodiester bridges or lipophilic and therapeutically effective nucleoside analogues are coupled to hydrophilic nucleotide derivatives.

Thus, the object of the present invention are amphiphilic nucleosidephosphate analogues of Formula I

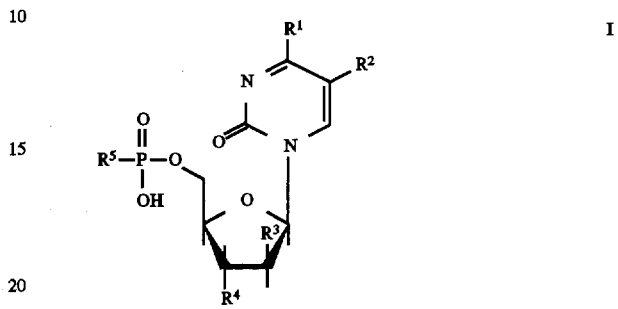

wherein $R^1$ stands for a hydroxyl-, amino-, acylated, or alkylized amino group or one substituted by polyoxyethylene, whose acyl- or alkyl rest is linear or branched, have 1 to 24 C-atoms and up to 2 double bonds, and which can be substituted by an aromatic radical;

$R^2$ stands for H, F, a 2-bromvinyl radical or a linear or branched $C_1$–$C_{14}$ alkyl radical;

$R^3$ and $R^4$ are identical or different and stand for H, hydroxyl, halogen and azido;

$R^5$ is a nucleoside radical of Formula II

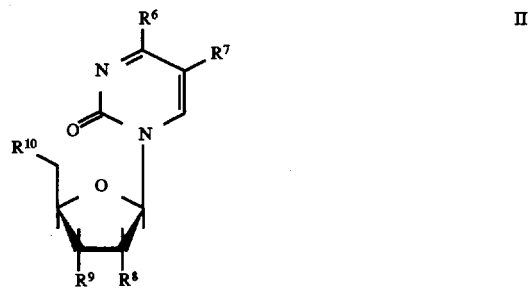

wherein $R^6$ is a hydroxyl-, amino-, acylated or alkylized amino group, whose acyl- or alkyl rest is linear or branched, which has 1 to 24 C-atoms and up to 2 double bonds, and which can be substituted by an aromatic radical, wherein $R^6$ and $R^1$ should be different;

$R^7$ stands for H, F, a 2-bromvinyl radical or a linear or branched $C_1$ to $C_{14}$-alkyl radical;

one of the radicals $R^4$ to $R^{10}$ is an oxygen atom that forms the bridge to the nucleotide of Formula I, the two remaining radicals are identical or different and stand for H, hydroxyl, halogen or azido;

$R^5$ can also be OH;

and the corresponding salts of the acid forms of these compounds.

If $R^1$ or $R^6$ is an alkylized amino group, then its alkyl radical is preferably a hexadecyl- or octadecyl radical.

If $R^1$ or $R^6$ is an acylated amino group, then its acyl radical is preferrably a palmitoyl-, oleoyl-, and behenoyl-(docosanoyl)radical.

Hydrogen, fluorine, methyl, and ethyl are preferred for $R^2$;

Hydrogen or a hydroxyl group are preferred for $R^3$, $R^4$, and $R^8$;

Hydrogen or a methyl group are preferred for $R^7$; and hydrogen, oxygen, or a hydroxyl group are preferred for $R^9$ and $R^{10}$.

F, Cl and Br are preferred as halogen substitutes. If $R^1$ or $R^6$ are aromatically substituted in the acyl- or alkyl radical, then this is preferably a phenyl substituent.

As has been pointed out above, according to the present invention, it is intended that the nucleoside radicals be so hydrophilic or lipophilic that the dinucleosidephosphate analogues display amphiphilic properties. For this reason, $R^1$ and/or $R^2$ represent lipophilic radicals and $R^6$ and/or $R^7$ stand for hydrophilic radicals or vice versa, or the radicals $R^1$, $R^2$, $R^6$, and $R^7$ are so selected that, together, they impart amphiphilic characteristics to the dinucleosidephosphate analogue.

The new amphiphilic dinucleosidephosphate analogues of Formula I can be produced in that compounds of Formula III

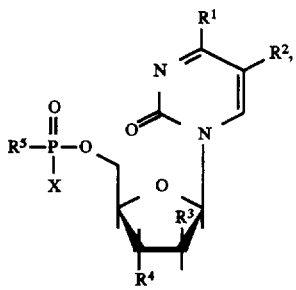

wherein $R^1$ to $R^5$ have the values quoted above, although $R^5$ does not stand for OH, and X is the chlorphenoxy radical or a hydrogen atom, a) are hydrolized if X is the chlorphenoxy radical, and the chlorphenyl radical is split off; or b) are oxidized if X stands for an H-atom.

The splitting off of the chlorated phenyl radical as in a) takes place particularly well if one allows a mixture of nitrobenzyldoxim and tetramethylguanidine to act on the compounds III, which can be dissolved in a mixture of organic solvents, for 0.5–2 hours, or allows tetrabutylammoniumfluoride to act on them for 45 minutes at room temperature.

The oxidation of the compounds III proceeds particularly well with iodine in organic-aqueous solvents at room temperature.

The production of compounds of Formula I, wherein $R^5$ stands for OH can be effected such that a compound of Formula V

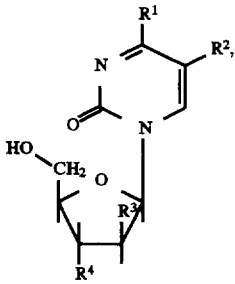

wherein $R^2$ to $R^4$ have the values already quoted, is phosphorylized selectively in the 5' position in the known manner or a compound of Formula Va

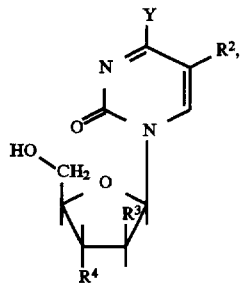

wherein $R^2$, $R^3$, and $R^4$ have the values already quoted and Y stands for a chlorine atom or the radical:

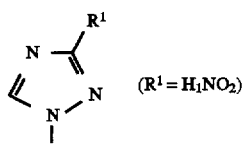

is converted with an amine of Formula Vb $$H_2N-R''$$  Vb wherein

R" is a linear or branched alkyl radical with 12 to 24 C-atoms, which has up to 2 double bonds, and can be substituted by an aromatic radical, and then optionally replaces the acetyl groups that are in the compound so obtained by H-atoms.

The reaction products so obtained can be purified by chromatography.

The compounds of Formula III that are used as starting material, in which X stands for chlorphenoxy, can be produced by condensation from compounds of Formula VI

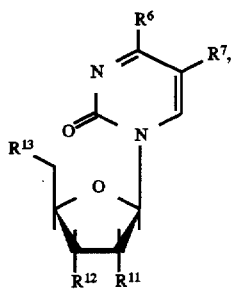

wherein $R^6$ and $R^7$ have the values already quoted, and $R^{11}$, $R^{12}$, and $R^{13}$ stand for H, azido, halogen, 4-monomethyoxytriphenylmethoxy, acetyl or 2-chlorphenylphosphate, one of these radicals always representing 2-chlorphenylphosphate, with compounds of Formula V

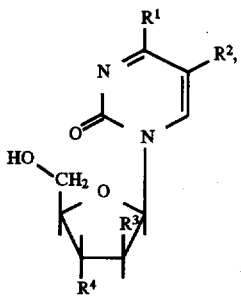

wherein

R¹ to R⁴ have the values already quoted, this being done in the known manner with the assistance of condensation means (Makromol. Chem. 188, 1313 (1987)). The 4-monomethoxytriphenylmethyl radical is then exchanged for hydroxyl under acidic conditions and the acetyl radical is exchanged for hydroxyl under alkyline conditions.

Compounds of Formula III that are used as starting material, in which X=H, can be produced in the known manner (Tetrahedron Lett. 27, 469 (1986)) by condensation of a compound of Formula VI

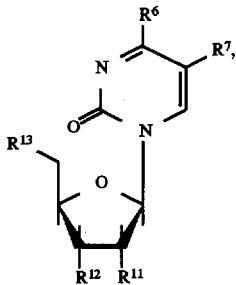

wherein

R⁶ and R⁷ have the values already quoted, R¹¹, R¹² and R¹³ stand for H, azido, halogen, 4-monomethoxytriphenyl-methoxyl, acetyl or hydrogen phosphonate, when one of the radicals R¹¹, R¹², R¹³ always stand for hydrogen phosphonate, with a compound of Formula V in the presence of an acidic chloride and then oxidation in the known manner (Tetrahedron Lett. 27, 469 (1986)). After oxidation and chromatographic processing, the 4-monomethoxytriphylmethyl- and/or acetyl radicals is exchanged for hydroxyl.

Naturally, the compounds of Formula III can be produced analogously to the above-described condensation in that the phosphate radical is made available through compounds of Formula V, one of the radicals R¹¹, R¹², R¹³ in Formula VI then standing for OH.

The starting materials that are required for the conversions are known substances or can be produced analogously to known procedures (J. C. S. Perkin I 1171 (1982); Makromol. Chem. 187, 809 (1986); Tetrahedron Lett. 27, 2661 (1986)).

The conversion of the therapeutically effective nucleoside analogues to amphiphilic dinucleosidephosphate analogues causes markedly changed pharmaco-kinetic behaviour, by means of which the dose that is to be applied can be increased in comparison to the particular monomer, without this simultaneously leading to an increase of all the toxic side effects of these highly potent medications.

The amphiphilic character of the nucleosidephosphate analogues according to the present invention permits various applications schemata. The lipophilic nucleoside components of the dinucleosidephosphate analogues results in the fact that the dimers together with matrix lipides can be incorporated in the lipid membrane of liposomes in a stable manner. The hydrophilic nucleoside components make it possible that the dimers are also water soluble, presumably by way of micelle formation. The lipophilic nucleoside component facilitates cell absorption of the amphiphilic dinucleosidephosphate analogues that are dissolved in the water and also protects them against excessively rapid enzymatic hydrolysis, so that the desired depot effect of the dimers is achieved not only in a liposome dispersion, but also in an aqueous solution. The alternative application of the amphiphilic dinucleosidephosphate analogues that is possible entails the advantage that one does not have to rely solely on liposome technology, although it can be used if required, which, once again, is not possible without problems in the case of dinucleosidephosphates that are only water soluble.

A further advantage of the amphiphilic dinucleosidephosphate analogues according to the present invention is that, together with one or more other substances, they can be incorporated in differing quantities in liposomes, this resulting in synergistic effects. The therapy used in cancerous diseases and infectious diseases caused by viruses can be optimized with these amphiphilic dinucleosidephosphate analogues and/or in combination with a biologically compatible carrier and/or with means that contain the compounds according to the present invention, at least in one or a plurality of combinations. Other compositions of a different type are prepared for the most effective possible application of the compounds according to the present invention. Common to all of these is the fact that the compounds according to the present invention are connected to an organic carrier.

A preferred embodiment of the compound provides for the association of the compounds according to the present invention in the form of mono to oligo-lamellar liposomes of the diameter of at most 0.4 μm. The compounds according to the present invention are integrated into the lipid double layer of the liposomes. All known procedures for liposome production such as, for example, ultrasound, gel-chromatography, detergent analysis, can be used to form the liposomes. The lipophile radicals that are introduced in each instance greatly influence the size and stability of the liposomes that are formed from the particular dinucleophosphate analogues together with other lipid components.

A further possibility for combining the compounds according to the present invention with an organic carrier is the inclusion of the compounds in a biologically compatible nanoparticle. Organo-chemical polymers to which the compounds according to the present invention are added during polymerisation so that they can be included into the nanoparticle with a specific efficiency are referred to as nanoparticles.

In one preferred embodiment, the compound is made with components that accumulate in the specific cells and/or organs that are to be treated. When this is done, the composition of the liposomes can be so selected that the liposomes can be additionally provided with molecules such as, for example, antibodies, charged lipids, lipids with modified hydrophilic head groups, so that the composition preferably accumulates in the cells and/or organs that are to be treated. Such a composition with molecules that are directed specifically against tumour cells, vitally infected cells and/or organs, increases the therapeutic effect of the medication and simultaneously reduces toxicity for non-infected tissue.

Compounds can be processed to form a substance that, in addition to the compounds according to the present invention and optionally to the organic carrier, also contains conventional carrier and/or diluting agents and/or secondary substances. Conventional carriers are, for example, glucose, dextrose, albumens, and the like, whereas physiological cooking salt solutions or a 5-% solution of glucose serve as diluting agents. In addition, it is usual to buffer these solutions with suitable reagents, for example phosphates. In addition, all other means that are usual in the preparation of pharmaceutical means can be added providing that they do not attack the compound made up of the organic carrier and the compounds according to the present invention. The means can be administered as an infusion solution as well as orally.

Not only are enzymatic resistance to hydrolysis increased but the forms of application greatly extended by the conversion to amphiphilic dinucleosidephosphate analogues; most surprisingly, cytostatic and virostatic effects are also optimized.

The amphiphilic dinucleosidephosphate analogues can also be used against malignant diseases of the blood-producing cells and other tumours.

Because of the improved cytostatic effect there are far fewer serious side effects and higher doses of the cytostatically effective compounds according to the present invention can be used, and therapy can be carried out in timed intervals.

Most surprisingly, the dinucleosidephosphate analogues also display virostatic effects so that they can be used in the chemotherapy applied for infections such as herpes and AIDS, which are caused by viruses.

The examples that follow describe the present invention.

EXAMPLE 1

The production of 2'-desoxythymidylyl-(3'-5')-$N^4$-palmitoyl-2',3'-didesoxycytidin.

a) Production of the starting material 5.5 g (7.4 mmol) of the barium salt of 5'-O-(4-monomethoxy)triphenylmethyl-2'-desoxyribothymidine-3'-O-(2-chlorphenyl)phosphate, together with 2.2 g (4.9 mmol) $N^4$-palmitoyl-2',3'-didesoxycytidin are dissolved in approximately 15 ml of water-free pyridine whilst excluding moisture, initially 2.0 g (6.4 mmol) 2,4,6-triisopropylbenzolsulfonic acid chloride, a few minutes later 1.6 ml (19.7 mmol) N-methylimidazole are added to the solution. Then the reaction mixture is agitated whilst excluding moisture for 40 minutes at room temperature and then 5 ml of water is added to it. The solution is concentrated in a vacuum, spun twice, with 50 ml of toluol on each occasion, absorbed in 50 ml of chloroform and then fractionated with a five stage chloroform/methanol-gradient. The product is elutriated after the fourth gradient step. After drying of the isolated eluate, one obtains 3.7 g 5'-O-(4-monomethoxy)-triphenyl-2'- desoxythymidylyl(2-chlorophenyl)-(3'-5')-$N^4$-palmitoyl-2',3'-didesoxycytidine in the form of solid white foam.

b) Production of the end product

The foam obtained as in a) above is added to a solution of 3.0 g (10 mmol) of tetrabutylammoniumfluoride in 180 ml tetrahydrofurane/pyridine/water; 8/1/1/; V/V/V and stirred for 45 minutes at room temperature. The solution is concentrated, spun twice with 50 ml of toluol on each occasion, and absorbed in 200 ml of ethylacetate. This results in a cloudy solution that contains no precipitate, however. This agitated with 100 ml of water. When it is agitated with saturated NaCl solution, the desired product precipitates out of the now clear organic phase in the form of white, flakey precipitate that is separated through a frit.

The process is repeated until no more product precipitates out of the ethylacetate solution. After drying the precipitate in an oil-pump vacuum, one obtains 2.2 g 5'-O-(4-monomethoxy)triphenylmethyl-2'-desoxythymidylyl-(3'-5') -$N^4$-palmitoyl-2',3'-didesoxycytidine as a white, crystalline powder.

In order to exchange the 4-monomethoxytriphenylmethyl group for hydroxyl, 50 ml of acetic acid/water; 8/2; V/V are added to the product and left to stand for approximately 20 minutes with occasional agitation, at 50° C. The solution is concentrated down to an oil that is absorbed in 20 ml of chloroform/methanol; 8/2; V/V and fractionated on a silica gel column with a 3-stage chloroform/methanol gradient. The product is elutriated after the third gradient stage. After drying of the isolated eluate, one obtains 1.3 g 2'-desoxythymidylyl-(3'-5')-$N^4$-palmitoyl-2',3'-didesoxycytidine as a white, fine crystalline powder (decomposition point >210° C.) that displays an $R_f$ value of 0.63 from a silica gel thin film plate in the chloroform/methanol; 6/4/V/V circulating agent system.

EXAMPLE 2

Production of $N^4$-hexadecyl-2'-desoxycytidylyl-(3'-5')-2',3'-didesoxycytidine.

a) Production of the starting material 30 ml water-free pyridine with 8 ml (64.5 mmol) trimethylacetic acid is added to 13.1 g (16.6 mmol) $N^4$-hexadecyl-5'-O-(4-monomethoxy)triphenylmethyl-2'-desoxycytidine-3'-O-hydrogenphosphonate and 5 g (11.1 mmol) $N^4$-palmitoyl-2',3'-didesoxycytidine whilst excluding moisture. The solution is stirred at room temperature for 10 minutes, rotated to form a syrup, and then spun twice with 50 ml of toluol to form an oil.

b) Production of the end product 0.2M iodine solution (tetrahydrofurane/pyridine/water; 18/1/1; V/V/V) is added to the oil obtained as in a) and left to stand for 40 minutes at room temperature. After this oxidation, the reaction batch is agitated with a mixture of 350 ml of chloroform and 350 ml 2% aqueous $NaHSO_3$ solution. The organic phase is washed twice with 100 ml saturated NaCl solution, dried over $Na_2SO_4$, concentrated to 100 ml in a vacuum, and then fractionated on a silica gel column in a three-stage chloroform/methanol gradient. The desired product is elutriated after the third gradient stage. The isolated eluate is concentrated in a vacuum to form a syrup.

In order to exchange the 4-monomethoxy-triphenylmethyl group for hydroxyl, the syrup is treated with 50 ml of acetic acid/water; 4/1; V/V for 12 hours at room temperature and then purified on a silica gel column. The eluate that is isolated when this is done is once again concentrated to form a syrup, absorbed in 50 ml methanol that is saturated with ammonia, and left closed for 12 hours at room temperature. After renewed chromatographic purification on silica gel and processing of the isolated eluate, one obtains $N^4$-hexadecyl-2'-desoxycytidylyl-(3'-5') -2',3'-didesoxycytidine as a white, finely crystalline powder that decomposes above 180° C. and displays an $R_f$ value of 0.39 in the chloroform/methanol; 7/3; V/V circulating agent system.

EXAMPLE 3

Production of $N^4$-hexadecyl-2'-desoxycytidylyl-(3'-5')-5-ethyl-2'-desoxyuridine.

a) Production of the starting material 5.1 g (5.4 mmol) of the sodium salt of $N^4$-hexadecyl-5'-O-(4-monomethoxy)triphenylmethyl-2'-desoxycytidine-3'-

O-(2-chlorphenyl)phosphate is condensed together with 1.4 g (5.4 mmol) 5-ethyl-2'-desoxyridine as in Example 1. The condensation mixture is chromatographically purified on a silica gel column with chloroform.

b) Production of the end product

The foam obtained as in a) is treated for 90 minutes at room temperature with 20 ml of a solution of the following composition. 10 g of nitrobenzaldoxime and 5 ml tetramethylguanidine are dissolved in 80 ml chloroform/methanol; 9/1; V/V. After the reaction, the mixture is fractionated on a silica gel column with chloroform/methanol gradient. The isolated eluate is concentrated in a vacuum to form a syrup. In order to exchange the 4-monomethoxytriphenylmethyl group for hydroxyl, the syrup is treated with 50 ml acetic acid/water; 4/1 for 12 hours at room temperature. The solution is concentrated down to form a syrup in a rotation evaporator and absorbed in 5 ml methanol. The desired product is precipitated out by dropping in 100 ml of ether. Precipiate is vacuum filtered, dried, absorbed in 25 ml of chloroform and once again fractionated on a silica gel column with chloroform/methanol. The product that is isolated in this way is absorbed in 5 ml of water and chromatographized on a Sephadex G-10 column with water. The eluate that contains the product is lyophilized, whereupon $N^4$-hexadecyl-2'-desoxycytidylyl-(3'-5')-5-ethyl-2'-desoxyuridine is obtained, this displays an $R_f$ value of 0.54 and a decomposition point of >169° C. in the circulating agent system chloroform/methanol; 1/1; V/V.

EXAMPLE 4

Production of $N^4$-hexadecyl-5-methyl-3'-azido-2',3'-didesoxycytidine (abbreviated to hxd$^4$m$^5$AzddCyd hereinafter).

a) Production of the starting compound 4-(1,2,4-triazole-1-yl)-5-methyl-1-(B-D-3'-azido-5'-O-acetyl-2',3'-didesoxyribofuranosyl-2(1H)-pyrimidinon.

13.4 g (50 mmol) of commercial 2'-azido-2',3'-didesoxythymidine (AZT) is stirred in 100 ml of water-free pyridine with 23.5 mol (250 mmol) acetic acid anhydride for 5 hours at room temperature; 20 ml of methanol is added to it and it is once again stirred for 15 minutes. The solution is concentrated down to form a syrup in a rotation evaporator, and is rotated with toluol to remove the pyridine. The residue is absorbed in 160 ml water-free acetonitrile and then added drop by drop to the reaction solution described below.

31.1 g (450 mmol) 1,2,4-triazole is suspended in 260 ml water-free acetonitrile, 8.8 ml (96 mmol) phosphorylchloride is added to it and it is cooled in an ice bath to approximately 4° C. 60 ml (430 mmol) triethylamine and then the above solution of the AZT derivate are added drop by drop to the cooled reaction mixture within a period of 1 hour whilst it is being vigorously stirred. The ice bath is then removed and the reaction mixture is stirred for a further 45 minutes. The precipitate is suction filtered, washed twice, with 50 ml of acetonitrile on each occasion, and rejected. 45 ml triethylamine and 12 ml of water are added to the filtrate, concentrated after 10 minutes to approximately 50 ml in a vacuum, and then agitated with 600 ml chloroform, 500 ml 2%-aqueous sodiumhydrogencarbonate solution. The aqueous phase is extracted twice with 100 ml of chloroform on each occasion, the combined chloroform phases are concentrated down to form a syrup in a rotation evaporator, and this is then dissolved with approximately 300 ml of ethanol and heated. On cooling down, the desired product crystallizes out and is re-crystallized from 150 ml ethanol. After drying in a vacuum, 14.7 g (41 mmol) of white crystals (Fp. 143°–144° C.) is obtained.

b) Production of the end product

Within a period of 1 hour, 13.5 g (55 mmol) hexadecylamine, dissolved in 120 ml ethanol is added, drop by drop, to the synthesis product as in a) that is dissolved in 120 ml dioxane, at room temperature. The reaction batch is stirred for 1.5 hours, then concentrated in a vacuum to form a syrup and absorbed in 500 ml methanol that is saturated with ammonia, at room temperature. The well closed reaction batch is left to stand for 12 hours at room temperature, concentrated in a vacuum to form a syrup, and then chromatographically purified on a silica gel column with a chloroform/methanol gradient. The fractions of the desired product are freed of the solvent in a vacuum. When this is done, one obtains 16.0 g $N^4$-hexadecyl-5-methyl-3'-azido-2,3'-didesoxycytidine as a syrup that displays an $R_F$ value of 0.52 on the silica gel plate in the chloroform/methanol; 9/1; V/V system. In FD-mass spectroscopy, a value of 491.1 is found for the molecule peak +H and this confirms the calculated molecular mass of 490.7.

EXAMPLE 5

Production of $N^4$-palmitoyl-2',3'-dideoxycytidine-5'-phosphate.

2.7 g (6 mmol) $N^4$-palmitoyl-2',3'-dideoxycytidine is added gradually to a mixture of 1.09 ml (12 mmol) phosphorylchloride and 20 ml trimethylphosphate that is stirred at 0° C. The batch is stirred for a further 2 hours when cold and then slowly neutralized with 0.5N NaOH during cooling. The precipitate that is formed is centrifuged off, absorbed in chloroform/methanol; 7/3; V/V, filtered over sodium sulphate and freed of solvent in a vacuum. The residue so obtained is crystallized several times from ethanol. When this is done, 2.5 g of $N^4$-palmitoyl-2',3'-dideoxycytidine-5'-phosphate is obtained and this displays an $R_f$ value of 0.35 on the silica gel plate in the chloroform/methanol; 1/1; V/V system.

EXAMPLE 6

Production of $N^4$-palmitoyl-2'-desoxyribocytidylyl-(3'-5')-3'-azido-2',3'-didesoxythymidine (hereinafter abbreviated to $N^4$-palmitoyldC-AZT).

a) Production of the starting material 8.0 g (10 mmol) $N^4$-palmitoyl-5'-O-(4-monomethoxy)triphenyl-methyl-2'-desoxyribocytidine-3'-O-hydrogenphosphate and 2.7 g (10 mmol) 3'-azido-2',3'-didesoxythymidine was mixed in 30 ml of water-free pyridine with 6.2 ml (50 mmol) trimethylacetic acid chloride whilst excluding moisture. The solution was stirred at room temperature for 10 minutes, rotated to form a syrup, and then rotated with 20 ml toluol.

b) Production of the end product

The residue obtained as in a) is mixed with 100 ml of a 0.2M iodine solution (tetrahydrofurane/pyridine/water; 18/1/; V/V/V) and left to stand for 40 minutes at room temperature. After this oxidation, the reaction batch is agitated with a mixture of 350 ml chloroform and 350 ml of a 2%-aqueous $NaHSO_3$ solution. The aqueous phase was dried over $Na_2SO_4$, concentrated to up to 50 ml of chloroform in a vacuum, fractionated on a silica gel column in chloroform/methanol gradient. The fractions of the desired product which left the column with chloroform/methanol; 9/1; V/V were combined, concentrated to dryness and then crystallized out from methanol.

In order to exchange the t riphenylmethoxy groups for hydroxyl groups, the precipitate that was obtained was stirred for 12 hours at room temperature. The solution was then rotated in a vacuum until dry. The residue was absorbed in a little methanol and precipitated in ether by being added drop by drop.

The precipitate was drawn off, dried in a vacuum, absorbed in chloroform and once again fractionated on a silica gel column with chloroform/methanol gradients. The fractionation of the desired product, which left the column with chloroform/methanol; 7/3; V/V was concentrated to a syrup, absorbed in a little water, and chromatographically purified on a Sephadex G-15 column. The product fractions were concentrated and the residue was crystallized out from ethanol. When this was done, 4.6 g (5.8 mmol) $N^4$-palmitoyl-2'-desoxyribocytidylyl-(3'-5')-3'-azido-2',3'-didesoxythymidine was obtained that displayed an $R_f$ value of 0.54 on the silica gel plate in the chloroform/methanol; 1/1; V/V circulating agent system.

EXAMPLE 7

Production of $N^4$-hexadecyl-2'-desoxyribocytidylyl-(3'-5')-3'-azido-2',3'-didesoxythymidine (hereinafter abbreviated to $N^4$-hexadecyldC-AZT).

a) Production of starting material 9.4 g (10 mmol) of the sodium salt of $N^4$-hexadecyl-5'-O-(4-monomethoxy)triphenylmethyl-2'-desoxyribocytidine-3'-O-(2 chlorophenyl)phosphate and 2.7 g (10 mmol) 3'-azido-2',3'-didesoxythymidine were dissolved in 20 ml of water-free pyridine. Whilst excluding moisture, the solution was first mixed with 3.6 g (12 mmol) 2,4,6-triisopropylbenzosulphonic acid chloride and a few minutes later with 2.8 ml (36 mmol) N-methylimidazole. Then, whilst excluding moisture, the reaction mixture was stirred for 40 minutes at room temperature and 5 ml of water were added to it. The solution was concentrated in a vacuum, rotated out twice, on each occasion with 50 ml of toluol, absorbed in 30 ml of chloroform and then fractionated on a silica gel column with chloroform. The fractions of the desired product were concentrated in a vacuum to form a syrup.

b) Production of the end product

The syrup obtained as in a) was treated for 90 minutes at room temperature with 60 ml of a solution composed as follows: 10 g nitrobenzaldoxime and 5 ml tetramethylguanidine were dissolved in 80 ml chloroform/methanol; 9/1; V/V. Then the reaction mixture was fractionated on a silica gel column with chloroform/methanol gradients and processed further as in Example 6. After crystallization from ethanol, 2.6 g (3.3 mmol) $N^4$-hexadecyl-2'-desoxyribocytidylyl-(3'-5')-3'-azido-2',3'-didesoxythymidine was obtained, and this displayed an $R_f$ value of 0.56 in the chloroform/methanol; 1/1; V/V circulating agent system.

EXAMPLE 8

Production of a compound containing an organic carrier, one of the amphiphilic dinucleosidephosphate analogues according to the present invention, cholesterol and an antioxidant.

1. Composition of the liposomes

Liposomes with 10 mg of the compound according to the present invention per ml.

100 ml liposomes contain: 4.0 g phosphateidylcholine, 0.4 g cholesterol, 0.02 g a-DL-tocopherol, 1.0 g dinucleosidephosphate analogue dispersed in 0.9% cooking salt solution which, if necessary, are adjusted for example with phosphate buffer with a a desired pH value. In place of the optionally buffered cooking salt solution, 67 mM physiological phosphate buffer or a 5% glucose solution can be used.

2. Production

Production of 100 ml liposome dispersions that contain 10 mg of the compound according to the present invention per ml.

The lipides (4.0 g phosphateidylcholine, 0.4 g cholesterol, 0.02 g a-DL-tocopherol and 100 g amphiphile dinucleosidephosphate analogue are dissolved with a suitable quantity of methylene-chloride/methanol; 1/1; V/V (100 to 500 ml) in a 500 ml round flask. The organic solvents are removed in a rotation evaporator at 40° C. The resulting solvent-free lipid/effective substance mixture is solubilized by the addition of an appropriate quantity of 0.9% cooking salt that can be buffered, for example, with 10 mM phosphate buffer, in 100 ml. In place of the optionally buffered cooking salt solution, it is possible to use a 67 mM physiological phosphate buffer or a 5% glucose solution. The resulting so-called multi-lamellar liposomes can be further processed using a suitable process, e.g. , ultrasound, high pressure filtration, detergent dialysis, microemulsification, or other suitable methods.

EXAMPLE 9

Production of the liposome preparations by ultrasound.

In order to produce the liposome dispersions, 100 mg soya-phosphateidylcholine, 10 mg cholesterol, 1 mg a-DL-tocopherol, 7 mg $N^2$-palmitoyl-$N^6$-succinoyl-L-lysine and 2 to 12 mg of the amphiphilic dinucleosidephosphate analogues according to the present invention per ml are dissolved in chloroform/methanol; 1/1; V/V. 0.6 to 2.4 ml of this lipid strain solution are transferred to a lipid film in a reagent glass by infusion with air and then dried for approximately 1 hour at 50° C. in a vacuum. The lipid film is mixed with 3 ml 10 mM PBS (0.9% NaCl and 10 mM $NaH_2PO_4$, pH 7.3) and irradiated with the help of a microtip of a disintegrator for 30 minutes at 40 Watts. This forms an opalescent liposome dispersion.

Table 1

| Physico-chemical properties of liposomes (10 mg $N^4$-hexadecyldC-ATZ/ml) | | | |
|---|---|---|---|
| Production type | Hydrodynamic diameter (nm)[a] | Homogeneity[b] | Incorporation rate[c] in % |
| High pressure filtration | 170 | 0.52 | 95 ± 6 |
| Detergent dialysis | 22 | 0.40 | 98 ± 4 |
| Ultrasound | 86 | 0.56 | 100 |

[a] Hydrodynamic diameter and
[b] Homogeneity were determined by means of laser light dispersion. Homogeneity: 0.2 to 0.5 homogenous double film liposomes; >0.5 heterogenous populations of various sized liposomes. Reference measurements with homogenous latex spheres resulted in values from 0.2 to 0.5 homogeneity that corresponds to a normal Gaussian distribution with a small standard deviation.
[c] The incorporation rate of the $N^4$-hexadecyldC-AZT compound in the liposome double film was determined by UV spectrometry.

EXAMPLE 10

Production of the immunoliposomes.

1.2 nmol of an antibody as lyophilisate was mixed with 50 μl of the liposome preparation as in Example 7 and 7 mg (27 μmol) N(3-dimethylaminopropyl)-N'-ethylcarbodiimide× HCL (EDC) and adjusted to pH 4 by the addition of 30 μl PBS (pH 1). At hourly intervals, on two occasions, 7 mg EDC was added on each occasion. After approximately 5 hours stirring at room temperature, the reaction batch was applied to an ultrogel ACA 22 column and fractionated with PBS (pH 7.4). Fractions whose absorption rates correspond with the values of the liposome preparation was combined and used for cell targeting.

EXAMPLE 11

Anti-retroviral effect of $N^4$-hexadecyldC-AZT liposomes.

Experimental conditions

On day 0, 4 to $5 \times 10^4$ virus units (plaque forming units, see Ruprecht et al., Nature 323, 466, 1986) of the Rauscher leukemia virus were injected into Balb/C mice.

The doses set out in Table 2 were applied intraperitoneally or intravenously on days 1, 6, 11, 16.

TABLE 2

Conditions and results of intraperitoneal (ip) or intravenous (iv) therapy on days 1, 6, 11, 16 after viral infection with azidothymidine in phosphate buffer (A) or the $N^4$-hexadecyldC-AZT compound according to the present invention as liposome preparation (B).

| Effective agent | Dosage[a] in mg/kg bodyweight | Therapy | Spleen weight in mg ± SA[b] | I[c] in % |
|---|---|---|---|---|
| A | 380 | iv | 1.99 ± 0.35 | −5.9 |
| B | 380 | iv | 1.19 ± 0.19 | 48.4 |
| A | 380 | ip | 1.31 ± 0.09 | 31.6 |
| B | 407 | ip | 1.26 ± 0.51 | 37.5 |
| A | 760 | ip | 1.66 ± 0.26 | 9.7 |
| B | 814 | ip | 0.94 ± 0.25 | 60.2 |
| A | 1140 | ip | 1.59 ± 0.27 | 13.7 |
| B | 1221 | ip | 0.32 ± 0.06 | 93.9 |
| Controls | | | | |
| infected | — | ip | 1.79 ± 0.20 | 0 |
| uninfected | — | ip | 0.15 ± 0.03 | — |
| infected | — | iv | 1.86 ± 0.27 | 0 |
| uninfected | — | iv | 0.14 ± 0.05 | — |

[a]Dose related to AZT as active component of the $N^4$-hexadecyldC-AZT according to the present invention.
[b]SA, standard deviation.
[c]Inhibition of spleen enlargement calculated according to the formula given above.

Evaluation

On day 20 after viral infection, the mice were killed after anesthesia and the spleen removed immediately. Spleen weight was determined and the percentage inhibition of splenomegaly was determined according to the following formula:

$$I(\%) = [1 - X/(c-n)] \times 100,$$

wherein

I(%)=inhibition of splenomegaly in % x=median spleen weight of treated infected mice c=median spleen weight of untreated infected mice n=median spleen weight of untreated uninfected mice.

EXAMPLE 12

The virostatic effect of the new amphiphilic dinucleoside-phosphate analogues can be demonstrated in the following experimental set-up:

Mouse-embryo-cell cultures were infected with herpes simplex virus (HSV-1 or HSV-2). The amphiphilic dinucleosidephosphate analogues which were dissolved in concentrations of 500 µl/ml, 50 µl/ml, and 5 µl/ml in the medium were added to these cell cultures.

After three days of incubation, the virostatic effect was shown on the reduction of the plaque count. The new compounds display a greater effect as, for example, the known 5-ethyl-2'-desoxy-uridine virostatic.

We claim:

1. Amphiphilic nucleoside phosphate analogues of formula I (I)

wherein $R^1$ denotes a hydroxyl or amino group or an acylated or alkylated or polyoxyethylene-substituted amino group, the acyl or alkyl group of which is straight-chained or branched, has 1 to 24 carbon atoms and up to 2 double bonds and may be substituted by an aromatic group;

$R^2$ denotes H, F, a 2-bromo vinyl group or a straight-chained or branched $C_{1-24}$-alkyl group;

$R^3$ and $R^4$ are identical or different and denote H, hydroxyl, halogen and azido; $R^5$ denotes a nucleoside group of formula II (II)

wherein $R^6$ denotes a hydroxyl or amino group or an acylated or alkalized amino group, the acyl or alkyl group of which is straight-chained or branched, contains 1 to 24 carbon atoms and up to 2 double bonds and may be substituted by an aromatic group, whilst $R^6$ and $R^7$ are different and one of the groups denotes acylamino or alkylamino groups having 12 to 24 carbon atoms, $R^7$ denotes H, F, a 2-bromovinyl group or a straight-chained or branched $C_{1-24}$-alkyl group;

one of the groups $R^8$ to $R^{10}$ denotes an oxygen atom which forms the bridge to the nucleotide of formula I, the two remaining groups are identical or different and denote H, hydroxyl, halogen or azido; and $R^1$ and/or $R^2$ denote lipophilic groups as defined above for $R^1$ and/or $R^2$ and $R^6$ and/or $R^7$ denote hydrophilic groups as defined above for $R^6$ and/or $R^7$ or vice versa; or the groups $R^1$, $R^2$, $R^6$ and $R^7$ are selected so that, together, they impart an amphiphilic nature to a dinucleotide phosphate analogue; and the corresponding salts of the acid forms of these compounds.

2. Compounds according to claim 1, wherein $R^6$ denotes an octadecyl- or docosyl-amino group or a palmitoyl-, oleoyl- or behenoyl-amino group and $R^7$ and $R^8$ denote H.

3. Compounds according to claim 1, wherein
$R^1$ denotes an amino or hydroxyl group,
$R^2$ denotes an H-atom or methyl,
$R^3$, $R^4$, $R^9$ and $R^{10}$ are identical or different and represent H, hydroxyl, azide or halogen and
one of the groups $R^8$, $R^9$ or $R^{10}$ denotes an oxygen atom which forms the bridge to the nucleotide of formula I.

4. Compounds according to claim 1, wherein $R^3$ and/or $R^4$ denote H, hydroxyl and/or azido.

5. Compounds according to claim 2, wherein
$R^1$, $R^4$ denote hydroxyl,
$R^2$ denotes ethyl or fluorine,
$R^3$ denotes H and
$R^9$ or $R^{10}$ denote an oxygen atom which forms the bridge to the nucleotide of formula I.

6. Compounds according to claim 1, wherein
$R^6$ denotes hydroxyl,
$R^7$ denotes methyl,
$R^2$ denotes H or methyl and $R^8$ denotes H,
$R^3$ and/or $R^4$ denotes H, OH or azido and
one of the groups $R^9$, $R^{10}$ denotes an oxygen atom which forms the bridge to the nucleotide of formula I and the other group denotes H or OH.

7. Compounds according to claim 1, wherein
$R^1$ denotes a palmitoyl-, oleoyl- or behenoyl-amino group and
$R^3$ and/or $R^4$ denotes H or OH.

8. Compounds according to claim 1, wherein
$R^1$ denotes an octadecyl- or docosyl-amino group and $R^3$ and $R^4$ denote hydroxyl.

9. A pharmaceutically agent containing at least one compound according to claim 1 in a pharmaceutically-acceptable carrier or diluent.

10. The agent of claim 9, in conjunction with a pharmaceutically-acceptable formulating agent, or incorporated in liposomes.

11. Compounds according to claim 1, prepared by a process characterized in that compounds of formula III

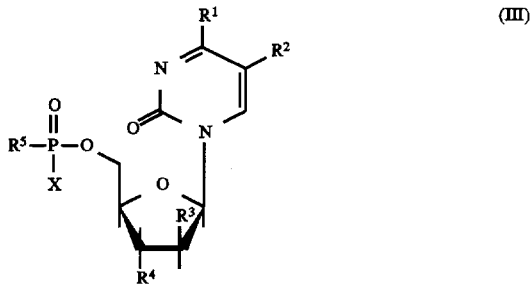

(III)

wherein
$R^1$ to $R^5$ are as hereinbefore defined but $R^5$ does not denote OH, and
X denotes the chlorophenoxy group or an H-atom,
  a) are hydrolyzed, if X denotes the chlorophenoxy group, and the chlorophenyl group is cleaved, or
  b) are oxidized, if X denotes an H-atom.

* * * * *